(12) United States Patent
Tigunait et al.

(10) Patent No.: US 7,771,757 B2
(45) Date of Patent: Aug. 10, 2010

(54) NASAL IRRIGATION SOLUTIONS AND METHODS OF USING SAME

(75) Inventors: Rajmani Tigunait, Honesdale, PA (US); James L. Miles, Honesdale, PA (US)

(73) Assignee: Himalayan International Institute of Yoga Science and Philosophy, Honesdale, PA (US)

( * ) Notice: Subject to any disclaimer, the term of this patent is extended or adjusted under 35 U.S.C. 154(b) by 172 days.

(21) Appl. No.: 12/189,959

(22) Filed: Aug. 12, 2008

(65) Prior Publication Data
US 2009/0035391 A1 Feb. 5, 2009

Related U.S. Application Data

(63) Continuation of application No. 10/630,166, filed on Jul. 30, 2003, now abandoned.

(60) Provisional application No. 60/400,304, filed on Jul. 31, 2002.

(51) Int. Cl.
*A01N 65/00* (2009.01)
(52) U.S. Cl. .................................................. 424/725
(58) Field of Classification Search ................ None
See application file for complete search history.

(56) References Cited

U.S. PATENT DOCUMENTS

| | | |
|---|---|---|
| 4,136,164 A | 1/1979 | Rowsell et al. |
| 4,150,052 A | 4/1979 | Watson et al. |
| 4,153,679 A | 5/1979 | Rowsell et al. |
| 4,230,688 A | 10/1980 | Rowsell et al. |
| 4,248,859 A | 2/1981 | Rowsell et al. |
| 4,318,900 A | 3/1982 | Rowsell et al. |
| 4,509,949 A | 4/1985 | Huang et al. |
| 4,534,960 A | 8/1985 | Chavkin |
| 4,883,660 A | 11/1989 | Blackman et al. |
| 4,980,169 A | 12/1990 | Oppenheimer et al. |
| 5,073,366 A | 12/1991 | Beck |
| 5,073,371 A | 12/1991 | Turner et al. |
| 5,087,445 A | 2/1992 | Haffey et al. |
| 5,116,311 A | 5/1992 | Löfstedt |
| 5,286,748 A | 2/1994 | Eby, III |
| 5,409,905 A | 4/1995 | Eby, III |
| 5,622,992 A | 4/1997 | Beck |
| 5,688,532 A | 11/1997 | Bryce-Smith |
| 5,851,556 A | 12/1998 | Breton et al. |
| 5,897,872 A | 4/1999 | Picciano |
| 6,103,218 A | 8/2000 | Brucker et al. |
| 6,116,468 A | 9/2000 | Nilson |
| 6,238,377 B1 | 5/2001 | Liu |
| 6,344,210 B2 | 2/2002 | Fust |
| 6,361,521 B1 | 3/2002 | Erickson |
| 6,365,624 B1 | 4/2002 | Davidson et al. |
| 6,387,416 B1 | 5/2002 | Newmark et al. |
| 2002/0004078 A1 | 1/2002 | Kleinberger et al. |
| 2002/0128273 A1 | 9/2002 | Kleinberger et al. |

OTHER PUBLICATIONS

Birdsall, Timothy C. Berberine: Therapeutic Potential of an Alkaloid Found in Several Medicinal Plants (n.d.). Downloaded from http://www.thorne.com/altmedrev/fulltext/berb.html on Jul. 17, 2002.
Richmond, Della. Goldenseal (n.d.). Downloaded from http://www.alveus.com/lionman/delilah/files/Goldseal.txt on Jul. 15, 2002.
Anon. Berberine (n.d.). Downloaded from http://throne.com/altmedrev/.fulltext/5/2/175.html on Jun. 29, 2002.
Cernakova, M. Potential antimutagenic activity of berberine, a constituent of *Mahonia aquifolium* (Feb. 2002). Downloaded from http://www.ncbi.nlm.hih.gov on Jun. 29, 2002.
Wang, S. Experimental study of bacteriostatic activity of Chinese herbal medicines on primary cariogenic bacteria in vitro (Sep. 2001). Downloaded from http://www.ncbi.nlm.hih.gov on Jun. 29, 2002.
Stermitz, Frank. Synergy in a medicinal plant: Antimicrobial action of berberine potentiated by 5'-methoxyhydnocarpin, a multidrug pump inhibitor (Feb. 15, 2000). PNAS, vol. 97, No. 4, pp. 1433-1437.

(Continued)

*Primary Examiner*—Michael V Meller
(74) *Attorney, Agent, or Firm*—Banner & Witcoff, Ltd.

(57) ABSTRACT

A nasal irrigation solution comprising is disclosed comprising water and hydrastine extracted from one or more plants. Another solution comprises water and berberine extracted from one or more plants. These solutions are provided from an extract of goldenseal plant. Solutions are also disclosed having canadine, canadaline, and hydrastidine, all extracted from the goldenseal plant. More general solutions are disclosed including alkaloids extracted from one or more plants. The alkaloids are selected from one or more of the group consisting of: berberine, oxyberberine, berbamine, palmatine, magnoflorine, phellodendrine, jateorrhizine, candicine, menisperine, coptisine, worenine, columbamine, epiberberine, hydrastine, canadine, canadaline, hydrastidine, oxycyanthine, berberrubine, and isotetrandine. Alkaloids are provided from plant from the group consisting of: Oregon grape root, yellow root, phellodendron bark, coptis rhizome, barberry root, and Indian barberry root bark. Other constituents may include extract of grapefruit seed, vegetable glycerine, salt, and water soluble zinc. A method for using these solutions is disclosed which includes flowing the solution through desired portions of nasal cavities.

13 Claims, 1 Drawing Sheet

OTHER PUBLICATIONS

Ellingwood, Finley. The American Materia Medica, Therapeutics and Pharmacognosy (1919). Downloaded from http://www.ibilbio.org/herbmed/eclectic/ellingwood/hydrastis.html Jul. 30, 2002.

Relaxant Effects of *Hydrastis canadensis* L. and its Major Alkaloids on Guinea Pig Isolated Trachea. Abdel-Haq Hanin et al *Pharmacology and Toxicology*, vol. 87, No. 5, Nov. 2000, pp. 218-222.

"Berberine" *Alternative Medicine Review: A Journal of Clinical Therapeutic*, Apr. 2000, vol. 5, No. 2, Apr. 2000, pp. 175-177.

"*Online*," Internet Article (anonymous), Mar. 14, 2001 (Retrieved from the Internet: http://web.archive.org/web/2002121115301/www.nutribiotic.com/Nasal+Spray.htm.).

"Indolopyridoquinazoline, Furoquinoline and Canthinone Type Alkaloids from *Phellodendron amurense* Callus Tissues." A Ikuta et al., Phytochemistry, *Pergamon Press*, GB, vol. 48 No. 2, May 1998. pp. 285-291.

"Herbal Medicine Goldenseal," N.W. Hamon, *Canadian Pharmaceutical Journal 1990*, Canada, vol. 123, No. 11, pp. 508-510.

Sack, RB et al. Berbine Inhibits Intestinal Secretory Response of *Vibrio cholerae* and *Escherichia coil* Enterotoxins Printed from http;://www.ncbi.nlm.nih.gov/entrez/query.fcgi?cmd=Retrieve&db=PubMed&list_uids=7035... last accessed on Jun. 29, 2002.

Ghosh, AK et al. Leishmania Donovani: Amastigote Inhibition and Mode of Action of Berberine Printed from http:// www.ncbi.nlm.nih.gov/entrez/query.fcgi?cmd=Retrieve&db=PubMed&list_uids=4076... last accessed on Jun. 29, 2002.

Soffar, SA et al. Evaluation of the Effect of a Plant Alkaloid (Berberine Derived from *Berberis aristata*) on *Trichomonas vaginalis* in Vitro Printed from http://www.ncbi.nlm.nih.gov/entrez/query.fcgi?cmd=Retrieve&db=PubMed&list_uids=1177... last accessed on Jun. 29, 2002.

Ivanovska, N. et al. Study on the Anti-Inflammatory Action of *Berberis vulgaris* Root Extract, Alkaloid Fractions and Pure Alkaloids Printed from http://www.ncbi.nlm.nih.gov/entrez/query.fcgi?cmd-Retrieve&db=PubMed&list_uids=9080... last accessed on Jun. 29, 2002.

Kaneda, Y. et al. Effects of Berberine, A Plant Alkaloid, on the Growth of Anaerobic Protozoa in Axenic Culture Printed from http://www.ncbi.nlm.nih.gov/entrez/query.fcgi?cmd=Retrieve&db=PubMed&list_uids=2131... last accessed on Jun. 29, 2002.

Cho, J.Y. et al. In Vitro Antiinflammatory Effects of Neolignan Woorenosides from the Rhizomes of *Coptis japonica* Printed from http://www.ncbi.nlm.nih.gov/entez/query.fcgi?cmd=Retrieve&db=PubMed&list_uids=1100... last accessed on Jun. 29, 2002.

Cho, J.Y. et al. Lignans from the Rhizomes of *Coptis japonica* Differentially Act as Anti-Inflammatory Principles Printed from http://www.ncbi.nlm.nih.gov/entez/query.fcgi?cmd=Retrieve&db=PubMed&list_uids=1145... last accessed on Jun. 29, 2002.

Goldenseal Printed from http:/./216.239.51.100/search?q=cache:znXCDpUn3nUC:www.sbwise.com/ingredients/golde... last accessed on Jul. 17, 2002.

Complementary and Alternative Therapies—Goldenseal Printed from http://216.239.51.100/search?q=cache:cXDnynM21_oC:www.susanlovemd.com/takecharge/... last accessed on Jul. 17, 2002.

*Rhizoma coptidis* (WHO—Manographs on Selected Medicinal Plants, pp. 105-114, publication dated prior to Aug. 12, 2008).

*Hydrastis canadensis* Printed from http://www.herbmed.org/Herbs/Herb83.htm last accessed on Jul. 17, 2002.

Eby, G.A. Zinc Ion Availability—The Determinant of Efficacy in Zinc Lozenge Treatment of Common Colds Antimicrob Chemother Oct. 1997;40(4):483-93 Printed from http://www.ncbi.nlm.nih.gov/entrez/query.fcgi?cmd=Retrieve&db=PubMed&list_uids=9371... last accessed on Jun. 29, 2002.

Prasad MD, Ananda S. et al. Duration of Symptoms and Plasma Cytokine Levels in Patients with the Common Cold Treated with Zinc Acetate—Annals of Internal Medicine 2000 American College of Physicians—American Society of International Medicine pp. 245-252.

Petrus, Edward J. et al. Randomized, Double-Masked, Placebo-Controlled Clinical Study of the Effectiveness of Zinc Acetate Lozenges on Common Cold Symptoms in Allergy-Tested Subjects Current Therapeutic Research, vol. 59, No. 9, Sep. 1998 Printed from http://www.coldcure.com/html/petrus595.html last accessed on Jun. 29, 2002.

Quick Review of Published Data for Common Cold Cure Printed from http://www.coldcure.com/html/review.html last accessed on Jun. 29, 2002.

Goldenseal (*Hydrastis canadensis* L.) Printed from http://ntp-server.niehs.nih.gov/htdoc/Chem_Background/ EXECSUMM/Goldenseal/Goldens... last accessed on Jul. 17, 2002.

Citricidal—Citricidal Technical Data Printed from http://ww.nutriteam.com/tech.htm last accessed on Jul. 17, 2002.

Citricidal Grapefuit Extract Minimum Inhibitory Concentration In-Vitro (MIC) Gram-Negative, Gram-Positive, Fungi & Yeasts, Other Organisms Printed from http://www.nutritream.com/MIC.html last accessed on Jul. 17, 2002.

Citricidal Grapefruit Seed Extract What Is It? Where Did it Come From? Printed from http://www.gfex.com/citricidal.htm last accessed on Jul. 17, 2002.

Grapefuit Extract: What Is It? Printed from http://www.nutriteam.com/gsewhat.html last accessed on Jul. 17, 2002.

How Was GSE Discovered? Printed from http://www.nutriteam.com/index2.html last accessed on Jul. 17, 2002.

NASAL IRRIGATION SOLUTIONS AND METHODS OF USING SAME

CROSS REFERENCE TO RELATED APPLICATIONS

This application is a continuation of U.S. Ser. No. 10/630,166, filed Jul. 30, 2003, pending, which claims benefit from provisional application 60/400,304, filed Jul. 31, 2002, which is now expired. The entire contents of these applications are incorporated herein by reference.

SUMMARY OF THE INVENTION

According to one aspect of the invention, a nasal irrigation solution is provided including water and hydrastine extracted from one or more plants.

According to another aspect of the invention a nasal irrigation solution is provided having water and berberine extracted from one or more plants.

According to another aspect of the invention, the alkaloids for these solutions is extracted from the Goldenseal plant. Advantageously, the extract of goldenseal may also provide canadine and canadaline, to the solutions.

According to another aspect of the invention, a nasal irrigation solution is provided to include water and alkaloids extracted from one or more plants.

According to another aspect of the invention, the alkaloids are selected from one or more of the group consisting of: berberine, oxyberberine, berbamine, palmatine, magnoflorine, phellodendrine, jateorrhizine, candicine, menisperine, coptisine, worenine, columbamine, epiberberine, hydrastine, canadine, canadaline, hydrastidine, oxycyanthine, berberrubine, and isotetrandine.

According to another aspect of the invention, the plants from which alkaloids are extracted are one or more of the group consisting of: Oregon grape root, yellow root, phellodendron bark, coptis rhizome, barberry root, and Indian barberry root bark.

According to another aspect of the invention, the solutions may include an extract of grapefruit seed, vegetable glycerine, or salt.

According to another aspect of the invention, any of the solutions may include water soluble zinc, preferably zinc acetate dihydrate, preferably in the range of about 2 to about 12 mg/ml.

According to another aspect of the invention, solutions are provided wherein the concentration of the solution for the plant extracts are: about 0.0001 to about 0.002 ml/ml for grapefruit seed extract; about 1 to about 10 mg/ml for phellodendron bark; about 1 to about 10 mg/ml for goldenseal root; about 1 to about 10 mg/ml for barberry root; and, about 1 to about 10 mg/ml for coptis rhizome.

According to another aspect of the invention, it was found beneficial to provide solutions having a family of alkaloids naturally occurring in plants. The family can comprise alkaloids collected from different plants. A family may also be defined from a group of alkaloids naturally occurring in a single plant. A family may be defined by a combination of inter and intra plant alkaloids.

According to another aspect of the invention, a family of alkaloids may be defined and provided as those alkaloids extracted by ethyl alcohol from one or more of the group of plants comprising: Oregon grape root, yellow root, phellodendron bark, coptis rhizome, goldenseal root, barberry root, and Indian barberry root bark.

According to another aspect of the invention a method of using these solutions to treat desired portions of a nasal passage or cavities is provided.

According to one method of the invention, any one of the solutions of the invention are flowed through at least a portion of the nasal cavities.

According to another aspect of the invention, the methods include diluting the solutions as desired into water or a saline solution to form a dilute solution and flowing the dilute solution through a desired portion of the nasal cavities.

According to another aspect of the invention, the flowing step includes feeding the solution into a first nostril while discharging the solution through a second nostril.

According to another aspect of the invention, the method includes placing the solution into a vessel having a port which cooperates with a first nostril to provide an acceptable degree of sealing between the vessel and the first nostril, and, positioning the nostril and the vessel with respect to each other such that either gravity or ambient air pressure will flow the solution from the vessel into the first nostril and out of a second nostril. In preferred embodiments, the flowing step includes flowing about 4 to about 16 ounces, and more preferably about the 8 ounces of solution, through the nasal cavities.

DETAILED DESCRIPTION OF A PREFERRED EMBODIMENT OF THE INVENTION

Figure 1:
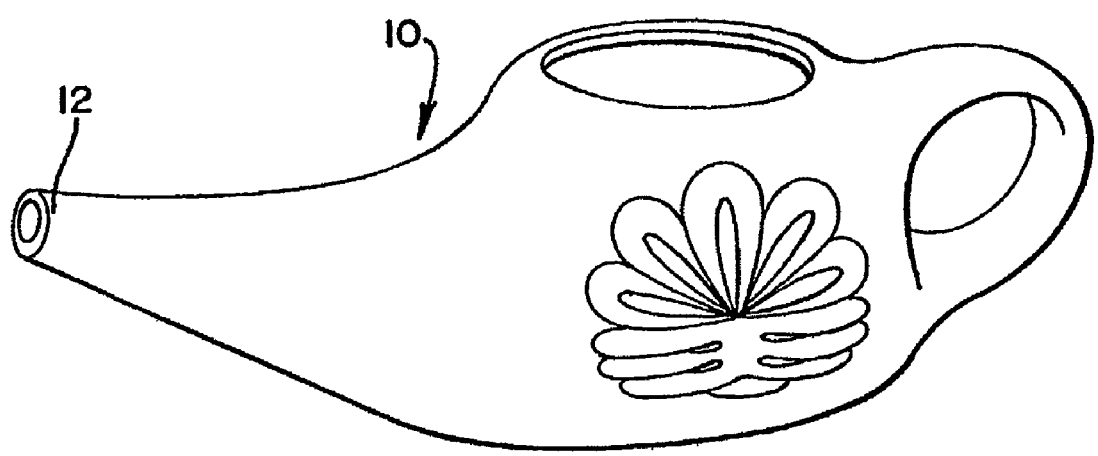
FIG. 1 is a side perspective or elevation view of a vessel for carrying out a method according to the invention; and, FIG. 2 is a side perspective or elevation view of the vessel of FIG. 1 in use according to the invention.

Preferred aqueous solutions according to the invention are disclosed. The solutions can be packaged in any size according to desire. However, according to the methods of the invention concentrated solutions are preferred. In the preferred example herein a two-ounce bottle is selected for distribution to consumers. The bottle contains 59 milliliters (ml) of solution. The concentrations for the preferred constituents will be given for the concentrated 59 ml solution. These concentrations will of course be different when and if a consumer dilutes the original solution according to preferred methods of use.

An exemplary solution contains 465 milligrams of Zinc Acetate U.S.P. or about 7.88 mg/ml of aqueous solution. The aqueous solution also contains: about 0.115 ml. of phellodendron bark (*phellodendron amurense*) extract which is about 2:1 weight to volume or 0.001955 ml/ml of solution; about 0.0385 ml of cultivated goldenseal root (*hydrastis canadensis*) extract (about 2:1 weight/volume) or 0.00065 ml/ml of solution; 0.0385 ml of barberry root bark (*berberis vulgaris*) extract (about 2:1 weight/volume) or about 0.00065 ml./ml.; about 0.0385 ml of coptis root (*coptis chinensis*) extract (2:1 weight/volume) or about 0.00065 ml/ml of solution; 0.05369 ml of grapefruit seed extract or about 0.00130 ml/ml of solution; about 0.02301 ml of glycerol (from vegetables); and, about 0.00039 ml/ml of solution.

The herbs or plants listed above are preferably, initially extracted with a hydro-alcoholic base (purified water and U.S.P. grade ethyl alcohol from corn) at a weight/volume ratio of about 1:4. The weight/volume ratio determines the strength of the herbal extract. A ratio of 1:4 is classified as a tincture. The tincture is then filtered and concentrated using a low-heat static process which removes all of the alcohol to a weight/volume ratio of 2:1. Then these extracts are blended (optionally with the other ingredients, such as zinc acetate dihydrate) very thoroughly in the base carrier ingredient which is preferably distilled, micro-filtered, ozonated water.

It will be understood by those of ordinary skill in the art that, the weight to volume ratio is a standard scale used to indicate the strength of a tincture or extract. Technically an extract is stronger than a tincture. The standard is represented by weight, which indicates the amount of herb material used to volume, which indicates the amount of menstrum or solvent (usually a mixture of water and grain alcohol of which the proportions are determined the sought after plant constituents). For example, a 1:1 weight to volume ratio indicates that 8.33 pounds of herb or botanical material is used per gallon of solvent, while a 2:1 weight to volume ratio indicates 16.33 pounds of herb is used per gallon of solvent. A 1:4 weight to volume ratio indicates that 8.33 pounds of herb is used per 4 gallons of solvent and so on.

Families of beneficial alkaloids for the solution may be derived (such as extracted by the above or other known means) according to the following naturally occurring families per plant, or combinations of alkaloids between plants (that is, their combination between alkaloids of different plants or "herbs"). For example, a naturally occurring family of alkaloids exist in each of the following plants (or herbs): Oregon grape root contains berberine, oxyberberine, and berbamine; yellow root contains berberine; phellodendron bark contains berberine, palmatine, magnoflorine, phellodendrine, jateorrhizine, candicine, and menisperine; coptis rhizome contains berberine, coptisine, palmatine, jateorrhizine, worenine, magnoflorine, columbamine, and epiberberine alkaloids; goldenseal root contains hydrastine, berberine, canadine, canadaline, and hydrastidine; barberry root contains berberine, oxycyanthine, berbamine, berberrubine, palmatine, isotetrandine, jateorrhizine, and columbamine; and, Indian barberry root bark contains berberine alkaloid.

Each of these plants contains its own family of alkaloids, and therefore according to the invention can provide a beneficial family on its own. Also, according to the invention, a mixture or family of alkaloids comprised of the alkaloids from differing plants can provide beneficial solutions.

It is also contemplated that the following constituents in various combinations with those claimed and disclosed herein would provide further advantages according to the invention for nasal treatment and solutions therefore: colloidal silver (at least 30-100 parts per million with a micron size of 0.001), pure sodium chloride (99.99% pure); and, essential oils of peppermint, eucalyptus, oregano, thyme, lemon, lime, orange, grapefruit, lemon grass, geranium, palma rosa, lavender, bergamot, pine, tea tree, sandalwood, and rosemary. Other herbs or their extracts such as *echinacea angustifolia*, *echinacea purpurea*, and *echinacea pallida* are also contemplated.

Numerous reports and studies show support for the antimicrobial activity of the major berberine containing plants. The berberine alkaloid has been shown to be active in vitro against the growth of organisms like streptococci, staphylococci, and pneumococci. Ethanol extracts of berberine containing plants have shown strong anti-inflammatory properties in many clinical investigations. Results from various clinical investigations into the major isolated alkaloids of Goldenseal root have provided a rational basis for the traditional antibacterial uses of this root.

While berberine and hydrastine, provide benefits according to the invention, it was discovered that the constituents disclosed herein provide synergistic compositions in which all of the ingredients compliment each other and work more effectively together than alone by themselves. For example, in the formulation and development of solutions according to the invention, it was also noted that with the addition of the Berberine containing herbs, the astringent qualities of the solutions increased. Subsequent inclusion of grapefruit seed extract in compositions incrementally increased the astringency level of the previous formula. In fact, each of the individual ingredients were used at one point individually during the earlier research stages and were empirically found to be less effective when used alone as opposed to a composition of two or more of the ingredients.

Various forms of Zinc were investigated in order to best scrutinize this element against human health ailments as well as effectiveness and stability in solutions according to the invention.

In certain preferred solutions according to the invention, Zinc plays several major roles functionally in the composition. Studies have shown that various types of Zinc help the body and immune system shorten the duration of common colds and reduce common cold symptoms while aiding in overall immune function. Zinc also assists and enhances the bodies' ability to heal wounds and maintain overall health and well being.

Much research has been done on zinc in variously administered forms and has demonstrated that zinc can cut the duration of common cold symptoms by half in many cases. This body of research on zinc has shown to speed the recovery of the physiology when invaded by a cold or flu. In-vitro laboratory studies have shown that zinc may interfere with the reproductive process of various viruses known to cause colds (i.e. rhinoviruses). Similar in-vitro inspections with zinc have shown that it may interfere with the ability of certain viruses to enter the cells of the body.

In use with the present invention, it was shown that zinc acetate in combination with the other constituents is more effective than other means of administration due to the direct topical application and saturation of portions of sinus physiology, which is achieved for at least 30 seconds when applied according to the methods of this invention. This direct saturation leads to greater astringency and mucosal absorption of zinc and the other components in the solution.

It was also discovered during the development of solution compositions according to the invention that having zinc in the solution and particularly zinc acetate, showed (through organolapetic means, primarily taste), that the solution was exceptionally astringent and drying.

Others have provided means for delivering various beneficial components to the nasal passages via sprays, inhalants, and the like. These methods are deficient at reaching many portions of the sinus and do not provide optimal exposure of the active ingredients to nasal tissue. Accordingly it was proposed to provide solutions according to the invention to the nasal passages by streaming the solutions into an out of the passages. It is proposed that, for a given total amount of active ingredient to be dosed to a nasal passage, exposure to the tissue is increased by diluting the amount in a solvent but then streaming the entire amount (as the dilute solution) over the desired nasal tissue.

FIG. 1 discloses a vessel 10 for practicing methods according to the invention. According to a preferred method of the invention, vessel 10 is filled with a diluent or carrier such as water or saline solution, and a desired amount of a solutions according to the invention is added. The resulting dilute solution is then flowed through at least a desired portion the nasal cavities.

Figure 2:
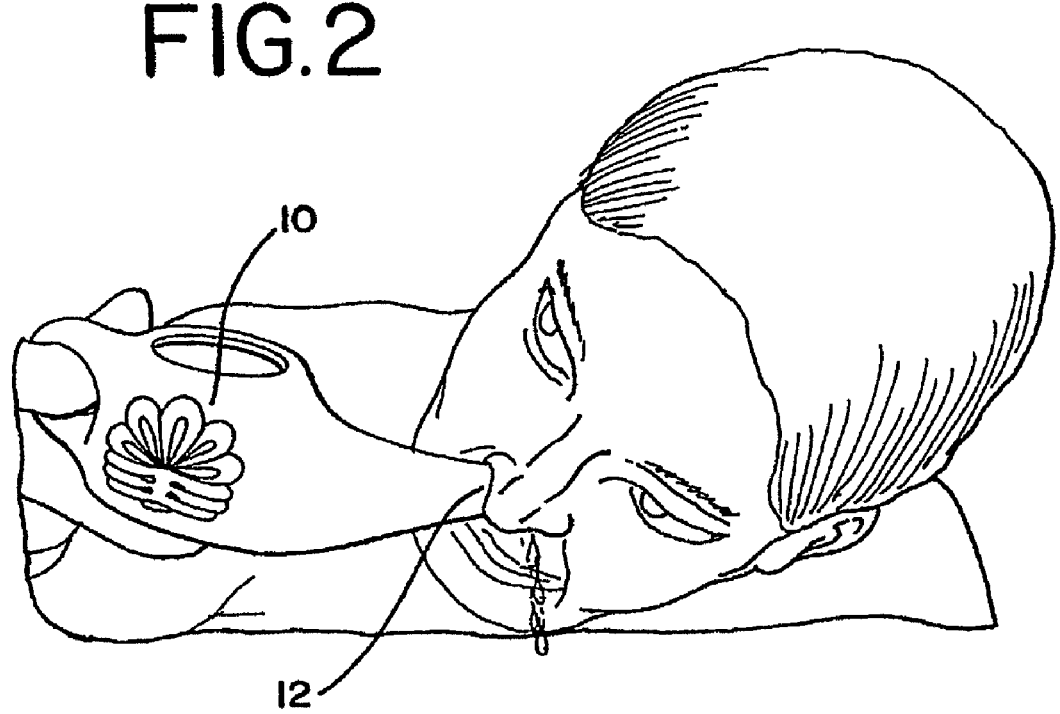

As disclosed in FIG. 2, a preferred method of irrigation includes flowing the solution into a first nostril while discharging the solution through a second nostril. The vessel 10 has a port or spout 12 which cooperates with a nostril to provide an acceptable degree of sealing between the vessel and the first nostril. The method includes positioning the nostril and the vessel 10, with respect to each other such that either gravity or ambient air pressure will flow the solution from the vessel 10 into the first nostril and out of the second nostril. The vessel 10 preferably hold about 8 oz of dilute solution, all of which is flowed through the nasal cavities. Using solutions of the concentrations disclosed herein, it is preferable to add between 1-10 ml, and more preferably about 3-5 ml, per 8 oz of diluent, such as for vessel 10.

Either larger vessels or repeated applications may be desired for additional irrigation.

We claim:

1. A method of treating nasal cavities comprising forming a nasal irrigation solution comprising water, water soluble zinc, and an alkaloid selected from the group consisting of canadine, canadaline and hydrastidine; and flowing the solution into the nasal cavities through a first nostril and discharging the solution through a second nostril.

2. The method of claim 1 further comprising diluting the solution into water or a saline solution to form a dilute solution and flowing the dilute solution.

3. The method of claim 1 further comprising placing the solution into a vessel having a port which cooperates with the first nostril to provide an acceptable degree of sealing between the vessel and the first nostril, and, positioning the first nostril and the vessel with respect to each other such that either gravity or ambient air pressure will flow the solution from the vessel into the first nostril and out of the second nostril.

4. The method of claim 1 further comprising flowing about 4 to about 16 ounces of the solution.

5. The method of claim 4 further comprising flowing about 8 ounces of the solution.

6. The method of claim 1 wherein the solution further comprises an extract of grapefruit seed.

7. The method of claim 6 wherein the extract of grapefruit seed comprises about 0.0001 to about 0.002 ml/ml of the solution.

8. The method of claim 1 wherein the solution further comprises vegetable glycerine.

9. The method of claim 1 wherein the solution further comprises salt.

10. The method of claim 1 wherein the water soluble zinc is zinc acetate.

11. The method of claim 10 wherein the zinc acetate is zinc acetate dihydrate.

12. The method of claim 10 wherein the zinc acetate is in the range of about 2 to about 12 mg/ml.

13. A method of treating nasal cavities comprising forming a nasal irrigation solution comprising water, zinc acetate dehydrate, an alkaloid selected from the group consisting of canadine, canadaline and hydrastidine, and an extract of grapefruit seed; and flowing the solution into the nasal cavities through a first nostril and discharging the solution through a second nostril.

* * * * *